United States Patent [19]

Neilson et al.

[11] Patent Number: 4,523,009

[45] Date of Patent: Jun. 11, 1985

[54] POLYPHOSPHAZENE COMPOUNDS AND METHOD OF PREPARATION

[76] Inventors: Robert H. Neilson; Patty J. Wisian-Neilson, both of 6513 Lawndale Dr., Fort Worth, Tex. 76134

[21] Appl. No.: 636,076

[22] Filed: Jul. 31, 1984

Related U.S. Application Data

[60] Continuation of Ser. No. 519,040, Aug. 1, 1983, abandoned, which is a division of Ser. No. 341,689, Jan. 22, 1982, Pat. No. 4,412,053, which is a continuation of Ser. No. 232,518, Feb. 9, 1981, abandoned.

[51] Int. Cl.³ ............................................. C08G 73/00
[52] U.S. Cl. .................................... 528/399; 528/30; 556/404
[58] Field of Search ................................ 525/399, 30

[56] References Cited

U.S. PATENT DOCUMENTS 4,182,837 1/1980 Hergenrother et al. ............ 528/399
4,242,494 12/1980 Hergenrother et al. ............ 528/399
4,258,171 3/1981 Hergenrother et al. ............ 528/399

FOREIGN PATENT DOCUMENTS 0019927 12/1980 European Pat. Off. ............ 528/399

OTHER PUBLICATIONS

"Polyphosphazenes: Part 1 Synthesis," Allen, Lewis & Todd, *Polymer II*, pp. 31 et seq. (1970).
"Polyphosphazenes: Synthesis—Properties—Applications," Singler, Schneider and Hagnawer, Polymer Engineering & Science, pp. 321 et seq. (1975).
Reaction of Poly(difluorophosphazene) with Phenyllithium," Allcock, Evans and Patterson, *Macromolecules*, vol. 13, pp. 201 et seq. 1980.
"Cross-Linking Mechanism in the Reactions of Poly(difluorophosphazene) with Alkyllithium Reagents," *Macromolecules*, vol. 14, pp. 218 et seq. (1981).
Preparation of Poly(diphenylphoshazene)," *Journal of Polymer Science*, vol. 6, pp. 3163 et seq. (1968).

*Primary Examiner*—Wilbert J. Briggs, Sr.
*Attorney, Agent, or Firm*—Charles D. Gunter, Jr.

[57] ABSTRACT

Shown are fully alkylated/arylated polyphosphazenes having side units bonded to the phosphorus backbone by direct carbon-phosphorus bonds. A method of preparing the polyphosphazenes includes the thermal decomposition of and elimination of silanes from suitably constructed N-silylphosphinimines.

4 Claims, No Drawings

POLYPHOSPHAZENE COMPOUNDS AND METHOD OF PREPARATION

The Government has rights in this invention pursuant to ARO Grant No. DDAG29-79-G-0004, awarded by the Department of the Army.

This application is a continuation of application Ser. No. 519,040, filed Aug. 1, 1983, now abandoned, which was a division of application Ser. No. 341,689, filed Jan. 22, 1982, now U.S. Pat. No. 4,412,053, which was a continuation of application Ser. No. 232,518 filed Feb. 9, 1981, now abandoned.

BACKGROUND OF THE INVENTION

This invention relates generally to novel polymeric phosphorus-nitrogen compounds and a method of preparing the same and, specifically, to polymeric phosphorus-nitrogen compounds having alkyl/aryl side units bonded directly to the phosphorus atoms through carbon-phosphorus bonds.

Synthetic polymers have revolutionized modern man's lifestyle in many ways, contributing greatly to the technological advances which have taken place in recent years. There exists a need, however, for new synthetic polymers having properties not found in conventional polymers having organic backbones. For example, most synthetic polymers having organic backbones burn and evolve smoke, reducing their desirability as textile fibers or household objects. Although flame retardant additives have been developed, these additives are expensive to use and often have toxic properties. Many of the known synthetic organic elastomers harden and degrade in the atmosphere, especially at high temperatures, and are attacked by oils, hydrocarbon fuels, and industrial solvents.

Although various inorganic backbone polymers have been investigated in the hope of overcoming these and other problems, only the silicones have achieved commercial significance to date. Inorganic backbone polymers based on alternating phosphorus and nitrogen atoms, referred to as polyphosphazenes, were at first thought to be cross-linked and hydrolytically unstable. Thus, although the thermal conversion of hexachlorocyclotriphosphazene to poly(dichlorophosphazene), also known as "inorganic rubber", has been known for over 80 years, the resulting material degrades with prolonged exposure to moisture, limiting its practical applications.

Attempts were made to stabilize poly(dichlorophosphazene) by replacing the chloride atoms with organic substituents. These attempts were unsuccessful until, in 1965, H. R. Allcock and his colleagues at Pennsylvania State University prepared stable polyphosphazenes by the melt ring opening polymerization of hexachlorocyclotriphosphazene (trimer) followed by reaction of the solution poly(dichlorophosphazene) which was formed with alkoxides such as sodium methoxide, ethoxide, or phenoxide, or with amines, such as aniline, piperidine or dimethylamine. The substituted products which resulted were hydrolytically stable elastomers or flexible thermoplastics of the general formula:

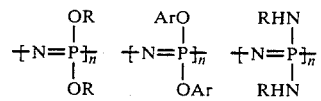

where R is an alkyl group, Ar is an aryl group, and "n" ranges as high as about 15,000.

The polyphosphazenes produced were hydrolytically stable but have side units bonded to the phosphorus atoms through oxygen or nitrogen atoms and not by direct carbon-phosphorus bonds. These phenoxy, alkoxy, or aryloxy side units are ionizable or displaceable and destabilize the polymers thermodynamically, leading to depolymerization at temperatures above about 200° C. Also, since the method involves first preparing a poly(dihalophosphazene) followed by nucleophilic displacement of the halogens along the chain, the substituents at phosphorus must be introduced after polymerization. It was not possible to incorporate the desired substituents before polymerization.

In 1977, Allcock and others succeeded in producing partially alkylated/arylated, mixed substituent polyphosphazenes of the general formula:

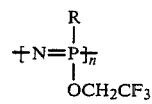

where R is alkyl/aryl and "n" is in the range of about 10,000 to 15,000. The method involved reaction of Grignard and other organometallic reagents with high molecular weight fluorocyclophosphazenes such as high molecular weight poly(difluorophosphazene). However, attempts to achieve full replacement of the fluorine resulted in shortening of the polymer chains. The polymers produced by this method continued to be subject to attack through the trifluoroethoxy side unit. Allcock's partially alkylated/arylated polymers were also marked by a random substitution pattern along the polymer backbone.

SUMMARY OF THE INVENTION

Shown are novel polymeric phosphorus-nitrogen compounds having alkyl/aryl side units bonded directly to the phosphorus atoms through carbon-phosphorus bonds having the formula:

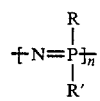

where R and R' are selected from the group consisting of alkyl, aryl, and lower alkyl-substituted aryl groups, said alkyl groups containing 1 to 5 carbon atoms and said aryl and alkyl-substituted aryl groups having 6 to 10 carbon atoms, and where "n" is greater then about 175. The novel compounds are linear, non cross-linked, polymers which are soluble in a series of common solvents.

A novel method for preparing the polymeric phosphorous nitrogen compounds involves the thermal decomposition of suitably constructed N-silylphosphinimines. A (disilylamino)phosphine is first reacted with bromine in benzene to eliminate bromotrimethylsilane and yield P-bromo-N-silylphosphinimines. The P-bromo-N-silylphosphinimines formed are then reacted with trifluoroethanol in the presence of triethylamine to give trifluoroethoxy substituted N-silylphosphinimines which are the precursors of the novel polymeric phosphorus-nitrogen compounds of the present invention. Upon heating the precursor, trifluoroethyoxytrimethylsilane is eliminated, producing fully alkyl/arylated polyphosphazenes.

Additional objects, features and advantages of the invention will become apparent in the following description.

DETAILED DESCRIPTION OF THE INVENTION

The method of preparing the polyphosphazenes of the present invention involves first producing P-bromo-N-silylphosphinimines. These compounds are prepared from another type of Si-N-P compound, the (disilylamino)phosphines. These compounds are known in the art and can be made, for example, as follows:

$$(Me_3Si)_2NH \xrightarrow{\text{n-BuLi}}_{Et_2O} (Me_3Si)_2NLi \xrightarrow{PCl_3}_{-78° C.}$$

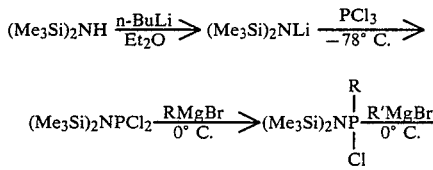

where R, R' = methyl, ethyl, and phenyl.

The (disilylamino)phosphine starting materials are then reacted with bromine in the presence of benzene as follows:

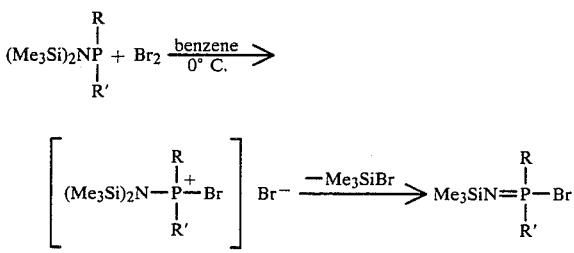

where R, R' = methyl, ethyl, phenyl, and trifluoroethoxy.

The reaction proceeds with the elimination of a silane, Me₃SiBr, yielding the desired P-bromo-N-silylphosphinimines. In the next step of the method, the P-Br bond is broken with Br being replaced by a trifluorethoxy group. This is preferably accomplished by reacting the P-bromo-N-silylphosphinimine with trifluoroethanol in the presence of triethylamine:

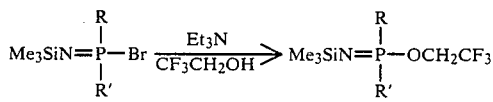

Alternatively, the P-bromo-N-silylphosphinimine can be reacted with lithium trifluoroethoxide in the presence of tetramethylethylenediamine (TMEDA) to eliminate lithium bromide.

The trifluoroethoxy substituted N-silylphosphinimines so produced are precursors of the novel polymeric phosphorous-nitrogen compounds of the present invention.

Upon heating the precursor, trifluoroethoxytrimethylsilane is eliminated as follows:

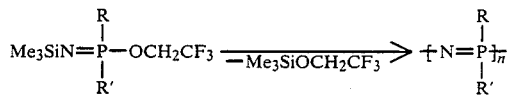

where R, R' = methyl, ethyl, and phenyl.

The novel polymeric nitrogen-phosphorous compounds formed have alkyl/aryl groups bonded directly to the phosphorus atoms by phosphorus-carbon bonds. The polymers are thus fully alkylated/arylated and are soluble in a series of common solvents such as CH₂Cl₂, CHCl₃, THF and ethanol. This characteristic of the new polymers distinguishes them from the older cross-linked phosphazenes which were insoluble in common solvents. The R and R' side units in the resulting polymer are determined at the outset by the makeup of the particular starting material utilized and are not randomly substituted along the polymer backbone. Generally, R and R' can be alkyl groups having 1 to 5 carbon atoms, and aryl and lower alkyl-substituted aryl groups having 6 to 12 carbon atoms, with "n" being greater than about 175. The compounds of the present invention are linear, noncross-linked polymers. Depending on the starting materials utilized, "n" will range between 175 and 1000, and even greater. Thus, as will be discussed in the examples, thermal decomposition of P-(trifluroethoxy)-P,P-dimethyl-N-(trimethylsilyl)-phosphinimine gives the dimethylphosphazene polymer which by light scattering techniques has a molecular weight of 50,000 corresponding roughly to an "n" of 650.

The decomposition of the trifluoroethoxy substituted N-silylphosphinimine occurs gradually at room temperature resulting in the dimethylphosphazene polymer being formed over several months time. The best results have been obtained by heating the precursor in the range of 150° to 200° C. for 20 to 48 hours. However, upon heating the precursor compound to 250° C. for 24 hours, only fluorotrimethylsilane was found in the volatile reaction products and a residual black solid was left in the reaction vessel. The decomposition time for other trifluoroethoxy substituted phosphinimine precursors has been found to vary between about 20 hours and three weeks depending upon the precursor chosen. Heating can be done in a bomb or in an open container under an inert atmosphere.

In the above method, P-bromo-N-silylphosphinimines were reacted with trifluoroethanol in the presence of triethylamine to give a suitably constructed trifluoroethoxy substituted N-silylphosphinimine precursor. Other N-silylphosphinimines can be prepared from the P-bromo compounds by reaction with various amines and alcohols. Thus, the P-bromo-N-silylphosphinimines react with dimethylamine and with alcohols in the presence of triethylamine to scavenge hydrogen bromide giving amino and alkoxy substituted phosphinimines:

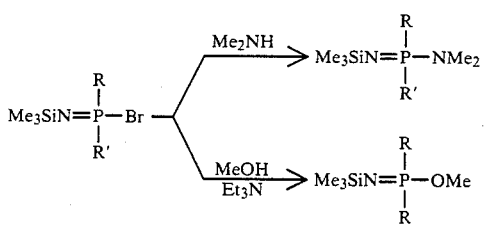

The amino and alkoxy substituted phosphinimines so produced differ from the precursor of the present novel polymer only in the nature of the leaving group, i.e., OMe, NMe$_2$ as opposed to OCH$_2$CF$_3$ in the polymer precursor. While the N-silylphosphinimines having F, Br, NMe$_2$, OSiMe$_3$, or OMe leaving groups are either stable compounds or thermally decompose to give exclusively cyclic phosphazenes, markedly different results are obtained when the leaving group is trifluoroethoxy. Thus, heating the P-bromo-P-P-dimethyl-N-silylphosphinimine gives only cyclic oligomers such as tetrameric dimethylphosphazene (Me$_3$PN)$_4$. Heating the trifluoroethoxy substituted N-silylphosphinimine precursor gives the polymeric phosphazene.

The following examples are provided to better illustrate the invention:

EXAMPLE 1

1. Preparation of (disilylamino)phosphines

A 5-liter, 3 neck flask was equipped with a paddle stirrer, nitrogen atmosphere, and an addition funnel. The flask was charged with (Me$_3$Si)$_2$NH (1.00 mole, 208.5 ml) and Et$_2$O(1.01). N-Butyllithuim (1.00 mole 1.6M hexane solution) was then added dropwise to the stirred solution at 0° C. The mixture was stirred for one hour at room temperature. The addition funnel was then washed with Et$_2$O (ca. 30 ml) and charged with PCl$_3$ (1.0 mole, 87.2 ml). The reaction flask was cooled to −78° C. and the PCl$_3$ was added dropwise. The mixture was then allowed to warm to room temperature and, after stirring for one hour, was cooled to 0° C. The addition funnel was again washed with Et$_2$O and then charged with MeMgBr (2.0 moles, 3.0M, Et$_2$O solution). The MeMgBr was added to the reaction mixture over a period of about two hours at 0° C. The mixture was then warmed to room temperature and stirred for three hours. Stirring was stopped and the solution was decanted into nitrogen-filled 2-liter flask. The solids were then washed twice with 500 ml portions of Et$_2$O. Solvent was removed from the combined decantates under reduced pressure and distillation of the residue then afforded (Me$_3$Si)$_2$NPMe$_2$ as a colorless liquid (166 g. 75.1% yield, b.p. 55°-60° C./3.4 mm).

2. Bromination of (disilylamino)phosphines

The (disilylamino)phosphine (30-50 mmol) and 75 ml of benzene were then placed in a two-necked round bottom flask equipped with a magnetic stirrer, nitrogen inlet, and an addition funnel. The solution was cooled to 0° C. and an equimolar amount of bromine in benzene (75 ml) was added dropwise. After the solution was stirred for at least one hour at room temperature, benzene and Me$_3$SiBr were removed under reduced pressure and the product purified by distillation was the desired P-bromo-N-silylphosphinimine.

3. Preparation of trifluoroethoxy substituted N-silylphosphinimine

A 2-liter, three neck flask was equipped with a paddle stirrer, nitrogen atmosphere, and dropping funnel. The flask was charged with the P-bromophosphinimine Me$_3$SiN=P(Br)Me$_2$ (59.6 g., 262 mmole), benzene (400 ml) and Et$_3$N (42 ml, 300 mmole). Trifluoroethanol (20.4 ml, 262 mmole) was then added to the stirred reaction mixture at 0° C. The mixture was warmed to room temperature, stirred for 18 hours, and filtered under nitrogen to remove Et$_3$NHBr. Solvent removal followed by distillation gave Me$_3$SiN=P(OCH$_2$CF$_3$)Me$_2$ as a colorless liquid 37.3 g., 49% yield, b.p. 50° C./10 mm).

4. Thermal decomposition of trifluoroethoxy substituted N-silylphosphinimines (a) Preparation of (Me$_2$PN)$_n$ A neat sample containing 6.74 grams of P-trifluroethoxy-P-P-dimethyl-N-(trimethylsilyl)phosphinimine was heated in vacuo in a heavy walled glass ampoule of approximately 15 ml size for 40 hours at 190° C. After the ampoule was opened, Me$_3$Si—OCH$_2$CF$_3$ was removed in vacuo leaving a gummy white solid which was dissolved in CH$_2$Cl$_2$ and removed from the ampoule. Solvent evaporation gave 2.02 grams (100% yield) of poly(dimethylphosphazene) as an opaque, flexible polymeric film. The polymer is soluble in a series of common solvents such as CH$_2$Cl$_2$, CHCl$_3$, and ethanol, but insoluble in water, acetone, THF, and hexane. A floculent, white, power-like form of the compound with a melting point of 148°-149° C. precipitates when a CH$_2$Cl$_2$ solution of the film is poured into hexane. By light scattering, the molecular weight is 50,000 corresponding to roughly 650 repeating units. The glass transition temperature of the polymer is −40° C.

Elemental analysis and IR and NMR spectra as shown in Table I are consistent with the formula:

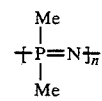

Characterization Data—TABLE I

Proton NMR (CDCl$_3$) 1.43 (d, J$_{PH}$=12.5 Hz);
Carbon-13 NMR (CDCl$_3$) 22.46 (d, J$_{PC}$=90.23 Hz);
Phosphorus-31 NMR (CDCl$_3$) 8.26;
IR, thin film, 1300(s), 1275(s), 1200(br,vs)cm$^{-1}$(P=N).

The NMR signals were all sharp lines and there was no indication of the presence of any small ring compounds such as (Me$_2$PN)$_{3,4}$.

(b) Preparation of [Me(Ph)PN]$_n$

A freshly prepared sample of the phosphinimine Me$_3$SiN=P(Ph)(OCH$_2$CF$_3$)Me (62 g., 201 mmole) was poured into a nitrogen-filled stainless steel reactor of about 300 ml capacity. The reactor was then evacuated and sealed by means of a stainless steel valve. The reaction vessel was then heated in an oven at 190° C. for 302 hours (12.6 days). During this time the reactor was occasionally cooled and opened in order to monitor the progress of the reaction by measuring the amount of Me$_3$SiOCH$_2$CF$_3$ produced. Decomposition was judged to be complete after 302 hours and, after removing Me$_3$Si—OCH$_2$CF$_3$ under vacuum, the reactor was opened and a dark brown polymer mass was observed. The product was dissolved in THF and purified by pouring into H₂O which produced rubbery, elastomeric strands of the polymer. After washing with acetone and drying, the material was identified as [Me(Ph)PN]$_n$ by elemental analysis and NMR spectra. By gel-permeation chromatography, the molecular weight is 53,900 corresponding to roughly 400 repeating units. The glass transition temperature of the polymer is 37° C.

The polyphosphazene compounds formed according to the present method are fully alkylated/arylated with direct carbon-phosphorus bonds on the phosphorus backbone. By removing the reaction pathways that existed in prior polyphosphazene compounds having side groups bonded to phosphorus through oxygen or nitrogen, a more thermodynamically stable polymer results. The method of preparation utilized affords excellent yields and utilizes a conveniently prepared starting material. The new polyphosphazenes are generally fire retardent and are water and oil repellant. Their low glass transition temperatures also make them well suited for oil resistant low temperature applications.

While the invention has been shown in only two of its forms, it should be apparent to those skilled in the art that it is not thus limited but is susceptible to various changes and modifications without departing from the spirit thereof.

We claim:

1. A linear non cross-linked phosphazene polymer, having the formula:

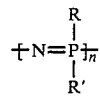

wherein
R is an alkyl group containing 1 to 5 carbon atoms and wherein R' is selected from the group consisting of alkyl, aryl, and lower alkyl-substituted aryl groups, said alkyl groups containing 1 to 5 carbon atoms, and said aryl and alkyl-substituted aryl groups having 6 to 10 carbon atoms;
n is greater than about 175; and
wherein both R and R' are bonded to phosphorus atoms by direct carbon to phosphorus bonds.

2. A linear non cross-linked phosphazene polymer, having, the formula:

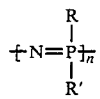

wherein
R is selected from the group consisting of methyl and ethyl and R' is selected from the group consisting of methyl, ethyl, and phenyl;
n is in the range of 175 to 1000; and
wherein both R and R' are bonded to phosphorus atoms by direct carbon to phosphorus bonds.

3. The linear phosphazene polymer of claim 2, wherein R and R' are methyl and n is approximately 650.

4. The linear phosphazene polymer of claim 2, wherein R is methyl, R' is phenyl and n is approximately 400.

* * * * *